(12) United States Patent
Ara et al.

(10) Patent No.: US 8,852,943 B2
(45) Date of Patent: Oct. 7, 2014

(54) METHOD OF MODIFYING TARGET REGION IN HOST DNA AND SELECTABLE MARKER CASSETTE

(75) Inventors: Katsutoshi Ara, Haga-gun (JP); Takuya Morimoto, Haga-gun (JP); Naotake Ogasawara, Ikoma (JP)

(73) Assignee: Kao Corporation, Tokyo (JP)

( * ) Notice: Subject to any disclaimer, the term of this patent is extended or adjusted under 35 U.S.C. 154(b) by 597 days.

(21) Appl. No.: 12/933,766

(22) PCT Filed: Mar. 23, 2009

(86) PCT No.: PCT/JP2009/056409
§ 371 (c)(1),
(2), (4) Date: Oct. 4, 2010

(87) PCT Pub. No.: WO2009/119862
PCT Pub. Date: Oct. 1, 2009

(65) Prior Publication Data
US 2011/0014709 A1 Jan. 20, 2011
US 2011/0275158 A2 Nov. 10, 2011
US 2013/0295676 A2 Nov. 7, 2013

(30) Foreign Application Priority Data
Mar. 24, 2008 (JP) ................. 2008-076008
Feb. 26, 2009 (JP) ................. 2009-044193

(51) Int. Cl.
*C12N 15/70* (2006.01)
*C12N 15/74* (2006.01)
*C12N 15/10* (2006.01)
*C12N 1/21* (2006.01)
*C07H 21/04* (2006.01)

(52) U.S. Cl.
CPC .......... *C12N 15/1082* (2013.01); *C12N 15/102* (2013.01)
USPC ................ 435/471; 435/252.3; 536/23.1

(58) Field of Classification Search
None
See application file for complete search history.

(56) References Cited

FOREIGN PATENT DOCUMENTS

JP 2007-111015 5/2007

OTHER PUBLICATIONS

Pedersen et al., Mol Microbiol., 45(2): 501-510, 2002.*
Yu et al., Nucl. Acids. Res., 36 (14): e84, pp. 1-8, 2008.*
Written Opinion and International Search Report for PCT/JP2009/056409, mailed Oct. 13, 2009, the European Patent Office, Munich, Germany.
Bloor, AE et al., "An Efficient Method of Selectable Marker Gene Excision by Xer Recombination for Gene Replacement in Bacterial Chromosomes," Appl. Envir. Microbiol 72: 2520-2525 (Apr. 2006), Am. Soc Microbiology, USA.
Fabret, C., et al., "A new mutation delivery system for genome-scale approaches in *Bacillus subtilis*," Mol Microbiol 46(1): 25-36 (Oct. 2002), Blackwell Publishing Ltd., England.
Liu, S, et al., "Introduction of marker-free deletions in *Bacillus subtilis* using the AraR repressor and the *ara* promoter," Microbiology 154: 2562-2570 (Sep. 2008), Society for General Microbiology, England.
Zhang, X-Z, et al., "*mazF*, a novel counter-selectable marker for unmarked chromosomal manipulation in *Bacillus subtilis*," Nucleic Acids Res., May 2006; 34: e71 (published online May 19, 2006), Oxford University Press, England.

* cited by examiner

*Primary Examiner* — Nancy T Vogel
(74) *Attorney, Agent, or Firm* — Sterne, Kessler, Goldstein & Fox P.L.L.C.

(57) ABSTRACT

A method of modifying a target region in a host DNA using a donor DNA: wherein the donor DNA having regions homologous to a 5'-side region outside of the target region in the host DNA, a 3'-side region outside of the target region in the host DNA and a first homologous recombination region inside of the target region in the host DNA, respectively, in this order, and further having a first selectable marker gene, an expression-inducing promoter and a second selectable marker gene expressed under the control of the expression-inducing promoter between the region homologous to the 3'-side region and the region homologous to the first homologous recombination region; which method has the steps of: a first step of performing homologous recombination between the donor DNA and the host DNA at the regions of the 5'-side region and the first homologous recombination region, to conduct selection of a host integrated with the donor DNA based on expression of the first selectable marker gene; and a second step of performing homologous recombination, within the host DNA integrated with the donor DNA by the first step, between two regions of the 3'-side region derived from the host DNA and the 3'-side region derived from the donor DNA, to conduct selection of a host whose target region is modified based on expression of the second selectable marker gene under an expression-inducing condition for the expression-inducing promoter; and a selectable marker cassette for use in the method.

9 Claims, 7 Drawing Sheets

SEQUENCE LISTING

```
<160> NUMBER OF SEQ ID NOS: 25

<210> SEQ ID NO 1
<211> LENGTH: 336
<212> TYPE: DNA
<213> ORGANISM: Escherichia coli
<220> FEATURE:
<221> NAME/KEY: CDS
<222> LOCATION: (1)..(336)

<400> SEQUENCE: 1 atg gta agc cga tac gta ccc gat atg ggc gat ctg att tgg gtt gat      48
Met Val Ser Arg Tyr Val Pro Asp Met Gly Asp Leu Ile Trp Val Asp
1               5                   10                  15 ttt gac ccg aca aaa ggt agc gag caa gct gga cat cgt cca gct gtt      96
Phe Asp Pro Thr Lys Gly Ser Glu Gln Ala Gly His Arg Pro Ala Val
            20                  25                  30 gtc ctg agt cct ttc atg tac aac aac aaa aca ggt atg tgt ctg tgt     144
Val Leu Ser Pro Phe Met Tyr Asn Asn Lys Thr Gly Met Cys Leu Cys
        35                  40                  45 gtt cct tgt aca acg caa tca aaa gga tat ccg ttc gaa gtt gtt tta     192
Val Pro Cys Thr Thr Gln Ser Lys Gly Tyr Pro Phe Glu Val Val Leu
    50                  55                  60
```

```
tcc ggt cag gaa cgt gat ggc gta gcg tta gct gat cag gta aaa agt      240
Ser Gly Gln Glu Arg Asp Gly Val Ala Leu Ala Asp Gln Val Lys Ser
 65                  70                  75                  80 atc gcc tgg cgg gca aga gga gca acg aag aaa gga aca gtt gcc cca      288
Ile Ala Trp Arg Ala Arg Gly Ala Thr Lys Lys Gly Thr Val Ala Pro
                 85                  90                  95 gag gaa tta caa ctc att aaa gcc aaa att aac gta ctg att ggg tag      336
Glu Glu Leu Gln Leu Ile Lys Ala Lys Ile Asn Val Leu Ile Gly
            100                 105                 110
```

<210> SEQ ID NO 2
<211> LENGTH: 111
<212> TYPE: PRT
<213> ORGANISM: Escherichia coli

<400> SEQUENCE: 2

```
Met Val Ser Arg Tyr Val Pro Asp Met Gly Asp Leu Ile Trp Val Asp
  1               5                  10                  15

Phe Asp Pro Thr Lys Gly Ser Glu Gln Ala Gly His Arg Pro Ala Val
                 20                  25                  30

Val Leu Ser Pro Phe Met Tyr Asn Asn Lys Thr Gly Met Cys Leu Cys
             35                  40                  45

Val Pro Cys Thr Thr Gln Ser Lys Gly Tyr Pro Phe Glu Val Val Leu
         50                  55                  60

Ser Gly Gln Glu Arg Asp Gly Val Ala Leu Ala Asp Gln Val Lys Ser
 65                  70                  75                  80

Ile Ala Trp Arg Ala Arg Gly Ala Thr Lys Lys Gly Thr Val Ala Pro
                 85                  90                  95

Glu Glu Leu Gln Leu Ile Lys Ala Lys Ile Asn Val Leu Ile Gly
            100                 105                 110
```

<210> SEQ ID NO 3
<211> LENGTH: 20
<212> TYPE: DNA
<213> ORGANISM: Artificial
<220> FEATURE:
<223> OTHER INFORMATION: Oligonucleotide as PCR primer pO2HC-lacF for
      amplification of lacI gene including a promoter

<400> SEQUENCE: 3
ctcacattaa ttgcgttgcg                                                 20

<210> SEQ ID NO 4
<211> LENGTH: 30
<212> TYPE: DNA
<213> ORGANISM: Artificial
<220> FEATURE:
<223> OTHER INFORMATION: Oligonucleotide as PCR primer pO2HC-lacR for
      amplification of lacI gene including a promoter

<400> SEQUENCE: 4
cttaccatag ttaatttctc ctctttaatg                                      30

<210> SEQ ID NO 5
<211> LENGTH: 30
<212> TYPE: DNA
<213> ORGANISM: Artificial
<220> FEATURE:
<223> OTHER INFORMATION: Oligonucleotide as PCR primer chpA-F for
      amplification of chpA gene

<400> SEQUENCE: 5
gaaattaact atggtaagcc gatacgtacc                                      30

```
<210> SEQ ID NO 6
<211> LENGTH: 33
<212> TYPE: DNA
<213> ORGANISM: Artificial
<220> FEATURE:
<223> OTHER INFORMATION: Oligonucleotide as PCR primer chpA-R for
      amplification of chpA gene

<400> SEQUENCE: 6
cgcggatcct acccaatcag tacgttaatt ttg                                33

<210> SEQ ID NO 7
<211> LENGTH: 22
<212> TYPE: DNA
<213> ORGANISM: Artificial
<220> FEATURE:
<223> OTHER INFORMATION: Oligonucleotide as PCR primer APNC-F for
      amplification of a cassette comprising a selection marker gene

<400> SEQUENCE: 7
cgacagcgga attgactcaa gc                                            22

<210> SEQ ID NO 8
<211> LENGTH: 20
<212> TYPE: DNA
<213> ORGANISM: Artificial
<220> FEATURE:
<223> OTHER INFORMATION: Oligonucleotide as PCR primer pro5-DF1 for
      amplification of 5' outer region

<400> SEQUENCE: 8
gagcaaagaa gagcgcatgg                                               20

<210> SEQ ID NO 9
<211> LENGTH: 31
<212> TYPE: DNA
<213> ORGANISM: Artificial
<220> FEATURE:
<223> OTHER INFORMATION: Oligonucleotide as PCR primer pro5-DR1 for
      amplification of 5' outer region

<400> SEQUENCE: 9
cagcatggag aagatttcaa cgtaattatg g                                  31

<210> SEQ ID NO 10
<211> LENGTH: 33
<212> TYPE: DNA
<213> ORGANISM: Artificial
<220> FEATURE:
<223> OTHER INFORMATION: Oligonucleotide as PCR primer pro5-DF2 for
      amplification of 3' outer region

<400> SEQUENCE: 10
cgttgaaatc ttctccatgc tgtgtgattg atc                                33

<210> SEQ ID NO 11
<211> LENGTH: 42
<212> TYPE: DNA
<213> ORGANISM: Artificial
<220> FEATURE:
<223> OTHER INFORMATION: Oligonucleotide as PCR primer pro5-DR2 for
      amplification of 3' outer region

<400> SEQUENCE: 11
ctgattgggt aggatccgcg atatttatcg acgaactcag at                      42
```

```
<210> SEQ ID NO 12
<211> LENGTH: 37
<212> TYPE: DNA
<213> ORGANISM: Artificial
<220> FEATURE:
<223> OTHER INFORMATION: Oligonucleotide as PCR primer pro5-IF for
      amplification of first recombination region

<400> SEQUENCE: 12
gagtcaattc cgctgtcgat caatcacaat ggaggac                              37

<210> SEQ ID NO 13
<211> LENGTH: 20
<212> TYPE: DNA
<213> ORGANISM: Artificial
<220> FEATURE:
<223> OTHER INFORMATION: Oligonucleotide as PCR primer pro5-IR for
      amplification of first recombination region

<400> SEQUENCE: 13
tacgtaagta tcagcacagg                                                 20

<210> SEQ ID NO 14
<211> LENGTH: 21
<212> TYPE: DNA
<213> ORGANISM: Artificial
<220> FEATURE:
<223> OTHER INFORMATION: Oligonucleotide as PCR primer pro5-checkF for
      amplification of a region to check a deletion of interest

<400> SEQUENCE: 14
ctgcaaaccc ataccttgca c                                               21

<210> SEQ ID NO 15
<211> LENGTH: 23
<212> TYPE: DNA
<213> ORGANISM: Artificial
<220> FEATURE:
<223> OTHER INFORMATION: Oligonucleotide as PCR primer pro5-checkR for
      amplification of a region to check a deletion of interest

<400> SEQUENCE: 15
catcactaaa tctcttaaac gtc                                             23

<210> SEQ ID NO 16
<211> LENGTH: 41
<212> TYPE: DNA
<213> ORGANISM: Artificial
<220> FEATURE:
<223> OTHER INFORMATION: Oligonucleotide as PCR primer flgB-F for
      amplification of flgB-fliH region

<400> SEQUENCE: 16
gcgttcagca acatgtctgt ttctcgacaa ggatattgag g                         41

<210> SEQ ID NO 17
<211> LENGTH: 40
<212> TYPE: DNA
<213> ORGANISM: Artificial
<220> FEATURE:
<223> OTHER INFORMATION: fOligonucleotide as PCR primer fliH-R for
      amplification of flgB-fliH region

<400> SEQUENCE: 17
gcagctgctt gtacgttgat ccgtaccgtt tatacgagtc                           40
```

<210> SEQ ID NO 18
<211> LENGTH: 20
<212> TYPE: DNA
<213> ORGANISM: Artificial
<220> FEATURE:
<223> OTHER INFORMATION: Oligonucleotide as PCR primer aprEclone-fF for
      amplification of 5' outer region

<400> SEQUENCE: 18
tctgatgtct ttgcttggcg                                           20

<210> SEQ ID NO 19
<211> LENGTH: 20
<212> TYPE: DNA
<213> ORGANISM: Artificial
<220> FEATURE:
<223> OTHER INFORMATION: Oligonucleotide as PCR primer aprEclone-fR for
      amplification of 5' outer region

<400> SEQUENCE: 19
acagacatgt tgctgaacgc                                           20

<210> SEQ ID NO 20
<211> LENGTH: 20
<212> TYPE: DNA
<213> ORGANISM: Artificial
<220> FEATURE:
<223> OTHER INFORMATION: Oligonucleotide as PCR primer aprEclone-bF for
      amplification of 3' outer region

<400> SEQUENCE: 20
atcaacgtac aagcagctgc                                           20

<210> SEQ ID NO 21
<211> LENGTH: 40
<212> TYPE: DNA
<213> ORGANISM: Artificial
<220> FEATURE:
<223> OTHER INFORMATION: Oligonucleotide as PCR primer aprEclone-bR for
      amplification of 3' outer region

<400> SEQUENCE: 21
ctgattgggt aggatccgcg ccattatgtc atgaagcacg                     40

<210> SEQ ID NO 22
<211> LENGTH: 38
<212> TYPE: DNA
<213> ORGANISM: Artificial
<220> FEATURE:
<223> OTHER INFORMATION: Oligonucleotide as PCR primer aprEclone-mF for
      amplification of first recombination region

<400> SEQUENCE: 22
gagtcaattc cgctgtcgtt ctcacggtac gcatgtag                       38

<210> SEQ ID NO 23
<211> LENGTH: 20
<212> TYPE: DNA
<213> ORGANISM: Artificial
<220> FEATURE:
<223> OTHER INFORMATION: Oligonucleotide as PCR primer aprEclone-mR for
      amplification of first recombination region

<400> SEQUENCE: 23
agaattaacg ctgctgctcc                                           20

```
<210> SEQ ID NO 24
<211> LENGTH: 20
<212> TYPE: DNA
<213> ORGANISM: Artificial
<220> FEATURE:
<223> OTHER INFORMATION: Oligonucleotide as PCR primer aprEclone-checkF
      for amplification of a region to check a deletion of selective
      marker and a insertion of flgB-fliH region

<400> SEQUENCE: 24
ttgcaaatcg gatgcctgtc                                               20

<210> SEQ ID NO 25
<211> LENGTH: 20
<212> TYPE: DNA
<213> ORGANISM: Artificial
<220> FEATURE:
<223> OTHER INFORMATION: Oligonucleotide as PCR primer aprEclone-checkR
      for amplification of a region to check a deletion of selective
      marker and a insertion of flgB-fliH region

<400> SEQUENCE: 25
tattgtggga tacgacgctg                                               20
```

METHOD OF MODIFYING TARGET REGION IN HOST DNA AND SELECTABLE MARKER CASSETTE

TECHNICAL FIELD

The present invention relates to a method of modifying a target region in a host DNA and relates to a selectable marker cassette.

BACKGROUND ART

Drug-resistance genes have been used as a means for artificial selection of transformants in the genetic engineering field. Specifically, a desired transformant can be selected based on a drug-resistance gene whose expression confers drug resistance. Not only the drug-resistance genes but also, for example, auxotrophic genes are used as means for selecting transformants. These genes usable for selecting transformants are generally called selectable markers (selectable marker genes).

Selectable marker genes are useful for selecting transformants. However, such a selectable marker gene, depending on its kind, unfavorably exhibits adverse effects on the environment, such as biological pollution of a wild-type microorganism by the selectable marker gene, if the selectable marker gene remains in a host cell. In addition, if multiple gene manipulations are performed on the same host, the kind of selectable marker genes that can be used may be limited. For that reason, it is desired to develop a means for removing the selectable marker gene from the transformant.

The selectable marker gene is also used when a mutant is constructed by deleting a particular region from a host genome or by inserting a foreign DNA into a host cell.

For example, JP-A-2007-111015 discloses a method for deleting a particular region in host genome by using a repressor and a promoter regulated by the repressor. Specifically, the method discloses that a DNA segment (donor DNA) is integrated into a host genome by homologous recombination, and then both of the donor DNA and the particular region of the host genome are deleted from the host genome by homologous recombination between a region of the donor DNA and a region of the host genome. In this method, the donor DNA contains a selectable marker and a gene encoding a repressor, and the host genome contains a promoter under the control of the repressor and a drug-resistance gene under the control of the promoter. A transformant in which the donor DNA is incorporated into the host genome can be selected by the selectable Marker derived from the donor DNA. In addition, when the donor DNA is integrated into the host genome, the host cell develops a drug-sensitivity by repressing expression of the drug-resistance gene. After the donor DNA is removed from the host genome, the expression of the drug-resistance gene is restored to give the drug-resistant host cell. As a result, it is possible to delete the particular region of the host genome without leaving the selectable marker derived from the donor DNA in the host genome.

As explained above, the method of JP-A-2007-111015 is advantageous in that the selectable marker gene can be used effectively. However, the method requires the additional step of introducing into the host genome beforehand an expression cassette which contains the promoter under the control of the repressor and the drug-resistance gene expressed under the control of the promoter.

In cloning a gene or a DNA segment, it is very difficult to insert a gene encoding a membrane protein, a gene encoding a protein that functions as a fatal factor in a host when the protein is present in a large amount (the presence of the protein in a large amount functions as a lethal factor in a host cell), a very large-sized DNA segment, and the like into a plasmid. When a plurality of genes are involved in a particular biosynthesis or a plurality of genes constituting a subunit, it is also difficult to insert these genes and express them in a cell, simultaneously. To overcome the problem of cloning such a gene or a DNA segment, a method of using a low-copy plasmid, a method of using a bacteriophage or a cosmid generally used for preparation of a genome library as a vector, and the like have been proposed. In addition, a method of using a promoter that can strictly regulate gene expression and a method of improving chaperone function of the host *Escherichia coli* have also been proposed.

However, the method of improving the host often depends on the specificity of the desired product, and requires the selection and adjustment of a cloning process suitable for the specificity. In the method of using the phage or cosmid, it is also difficult to insert a plurality of genes into a plurality of gene loci of a cell.

Accordingly, there is a desire for development of a method of inserting a plurality of and relatively large-sized DNA fragments into a single cell with a simple procedure compared with the conventional method of using a phage. In recent years, DNAs obtained from environmental materials are eagerly studied by means of metagenome analysis. There is a need for a new tool and a new method of cloning genes and DNA segments that are hard to clone by conventional methods.

SUMMARY OF INVENTION

As described above, the conventional genetic manipulation method for modifying a host DNA and obtaining a transformant has a problem that a selectable marker is left in the transformant.

The method of JP-A-2007-111015 contains the necessary step of introducing into the host genome beforehand the expression cassette. Thus, the method is not entirely satisfactory for improvement of operational efficiency. In addition, the expression cassette previously introduced is left behind in the host genome, even after the particular region is deleted from the host genome.

In the conventional genetic manipulation method using a plasmid, it is difficult to introduce a large-size DNA segment or a lethal gene into a desired region of a host DNA. Further, in the conventional method using a phage or cosmid, it is impossible to insert a plurality of genes into plural loci of a single cell.

The present invention is to provide a method of modifying a target region in a host DNA; in which the method enables to modify the target region in the host DNA with a simple procedure without limiting the kind of a selectable, marker (selectable marker gene) that can be used, and to modify the target region in the host DNA without leaving the selectable marker and the like used in modification steps in the modified host DNA; and to provide a selectable marker cassette for used therein.

Specifically, the present invention is to provide a method of modifying the host DNA by deleting the desired region in the host DNA, and, after deletion, yet not leaving the selectable marker gene and others in the host DNA. The present invention is also to provide a method of modifying the host DNA by replacing any region in the host DNA with a desired DNA sequence (particularly, for example, a large-sized DNA fragment, a DNA fragment that is hard to introduce into a host, or a plurality of genes (multiple genes)), and, after replacement, leaving only the desired DNA sequence inserted into the host DNA but not leaving the selectable marker gene and others.

According to the present invention, there is provided the following means:

A method of modifying a target region in a host DNA according to the present invention (hereinafter, referred to as the modification method of the present invention) is a method of modifying a target region in a host DNA using a donor DNA:

wherein the donor DNA comprising regions homologous to a 5'-side region outside of the target region in the host DNA, a 3'-side region outside of the target region in the host DNA and a first homologous recombination region inside of the target region in the host DNA, respectively, in this order, and further comprising a first selectable marker gene, an expression-inducing promoter and a second selectable marker gene expressed under the control of the expression-inducing promoter between the region homologous to the 3'-side region and the region homologous to the first homologous recombination region;

which method comprises the steps of:

a first step of performing homologous recombination between the donor DNA and the host DNA at the regions of the 5'-side region and the first homologous recombination region, to conduct selection of a host integrated with the donor DNA based on expression of the first selectable marker gene; and a second step of performing homologous recombination, within the host DNA integrated with the donor DNA by the first step, between two regions of the 3'-side region derived from the host DNA and the 3'-side region derived from the donor DNA, to conduct selection of a host whose target region is modified based on expression of the second selectable marker gene under an expression-inducing condition for the expression-inducing promoter.

A method of deleting a target region for deletion in a host DNA according to the present invention (hereinafter, referred to as the deletion method of the present invention) is a method of deleting a target region for deletion in a host DNA using a donor DNA:

wherein the donor DNA comprising regions homologous to a 5'-side region outside of the target region for deletion in the host DNA, a 3'-side region outside of the target region for deletion in the host DNA and a first homologous recombination region inside of the target region for deletion in the host DNA, respectively, in this order, and further comprising a first selectable marker gene, an expression-inducing promoter and a second selectable marker gene expressed under the control of the expression-inducing promoter between the region homologous to the 3'-side region and the region homologous to the first homologous recombination region;

which method comprises the steps of:

a first step of performing homologous recombination between the donor DNA and the host DNA at the regions of the 5'-side region and the first homologous recombination region, to conduct selection of a host integrated with the donor DNA based on expression of the first selectable marker gene; and a second step of performing homologous recombination, within the host DNA integrated with the donor DNA by the first step, between two regions of the 3'-side region derived from the host DNA and the 3'-side region derived from the donor DNA, to conduct selection of a host whose target region is deleted based on expression of the second selectable marker gene under an expression-inducing condition for the expression-inducing promoter.

A method of replacing a target region for replacement in a host DNA according to the present invention (hereinafter, referred to as the replacement method of the present invention) is a method of replacing a target region for replacement in a host DNA using a donor DNA:

wherein the donor DNA comprising regions homologous to a 5'-side region outside of the target region for replacement in the host DNA, a 3'-side region outside of the target region for replacement in the host DNA and a first homologous recombination region inside of the target region for replacement in the host DNA, respectively, in this order, comprising a desired DNA sequence between the region homologous to the 5'-side region and the region homologous to the 3'-side region, and further comprising a first selectable marker gene, an expression-inducing promoter and a second selectable marker gene expressed under the control of the expression-inducing promoter between the region homologous to the 3'-side region and the region homologous to the first homologous recombination region;

which method comprises the steps of:

a first step of performing homologous recombination between the donor DNA and the host DNA at the regions of the 5'-side region and the first homologous recombination region, to conduct selection of a host integrated with the donor DNA based on expression of the first selectable marker gene; and a second step of performing homologous recombination, within the host DNA integrated with the donor DNA by the first step, between two regions of the 3'-side region derived from the host DNA and the 3'-side region derived from the donor DNA, to conduct selection of a host whose target region is replaced with the desired DNA sequence based on expression of the second selectable marker gene under an expression-inducing condition for the expression-inducing promoter.

In the modification method, the deletion method and the replacement method of the present invention, the selection of the host in the second step based on expression of the second selectable marker gene can be made, for example, by positive selection.

Hereinafter, the host whose target region is modified, the host whose target region is deleted or the host whose target region is replaced with the desired DNA sequence will be referred to simply as "transformant" or "mutant".

In the modification method, the deletion method and the replacement method of the present invention, the second selectable marker gene is not particularly limited, but may be, for example, a gene encoding a protein that induces death of a host cell. The gene encoding a protein that induces death of a host cell is not particularly limited, but may be, for example, chpA gene.

In such a case, the host in which the selectable marker gene derived from the donor DNA is deleted from the host DNA through the second step can proliferate. On the other hand, the host having a genome retaining the selectable marker gene derived from the donor DNA is unable to proliferate under the expression inducing condition. The positive selection allows the selection of host having no selectable marker gene derived from the donor DNA.

In the modification method, the deletion method and the replacement method of the present invention, the expression-inducing promoter is not particularly limited, but may be a promoter which induces expression of a downstream gene in the presence of an expression inducer.

Further, in the modification method, the deletion method and the replacement method of the present invention, the first selectable marker gene is not particularly limited, but may be, for example, a drug-resistance gene. In particular, it is possible to prevent the selectable marker gene remaining in the host DNA, because the selectable marker gene is removed from the host DNA according to the modification method, the deletion method and the replacement method of the present invention.

Furthermore, in the modification method, the deletion method and the replacement method of the present invention, the kind of the host that can be used is not particularly limited, but may be, for example, *Bacillus subtilis.*

The selectable marker cassette for use in the present invention has the first selectable marker gene, the expression-inducing promoter and the second selectable marker gene expressed under the expression-inducing promoter. In the donor DNA, the selectable marker cassette lies between the region homologous to the 3'-side region outside the target region and the region homologous to the first homologous recombination region inside the target region.

The second selectable marker gene preferably encodes a protein that induces death of a host cell. In particular, chpA gene is preferably used as the second selectable marker gene. The expression-inducing promoter is preferably a promoter which induces expression of a downstream gene in the presence of an expression inducer. As the first selectable marker gene, a drug-resistance gene can be preferably used. The selectable marker cassette according to the present invention may be in the state incorporated in *Bacillus subtilis* genome.

Further, the present invention is to provide a method of producing a host modified a target region by using the above the modification method, the deletion method and the replacement method of the present invention.

According to the methods of the present invention, it is possible to modify the desired region in the host DNA with a simple procedure.

According to the present invention, neither the first selectable marker gene nor second selectable marker gene used in the modification process (including the deleting process and the replacing process) remain in the host DNA after modification. Accordingly, it is possible to prepare a desired transformant without limiting the range of the selectable marker genes that can be used. In particular when a plurality of regions in the host DNA are modified, the modifying process according to the present invention can be much simplified, compared with that by the conventional gene modification method that the selectable marker gene remains in the host, because any selectable marker gene can be used without restriction. In addition to the selectable marker gene, according to the present invention, the other regions (such as first homologous recombination region, promoter sequence, and the like) used in the modification process do not remain in the host DNA after modification. Thus, when a plurality of modification are repeatedly performed in the same host, the modification process according to the present invention can also be simplified.

Also, according to the present invention, it is possible to prevent the adverse effects on environment caused by residual of the selectable marker gene in the host. For example, if a drug-resistance gene is carried in a pathogenic strain (i.e., drug-resistant microbe), there is a concern about contamination of environment. The strain introduced with the drug-resistance gene is usually treated as a recombinant organism, and it demands to prevent the strain from spreading into the environment. Thus, the operation steps using such a strain more complicated, such as restriction in handling in production, use and storage of the strain, and demand to prevent diffusion of the strain. The present invention is effectively used for such the environmental containment caused by residual of the selectable marker gene.

Further, according to the present invention, the target region for modifying is not restricted to a particular position in the host DNA, and any region in the host DNA can be modified as the target region for modifying.

Furthermore, according to the present invention, over a wide region in the host DNA can be used as the target region for modifying. More specifically, a wide region in the host DNA can be deleted or replaced.

Other and further features and advantages of the invention will appear more fully from the following description, appropriately referring to the accompanying drawings.

MODE FOR CARRYING OUT THE INVENTION

Hereinafter, the present invention will be described in detail with reference to drawings.

In the present invention, the term "modifying a target region in a host DNA" means that a DNA sequence of the target region in the host DNA is altered or modified. Specifically, it means that the DNA sequence of the target region is deleted from the host DNA, or that the DNA sequence of the target region in the host DNA is replaced with the desired DNA sequence to insert the desired DNA sequence into the host DNA. Therefore, the modifying method of the present invention includes the deletion method of the present invention and the replacement method of the present invention as preferable embodiments. Hereinafter, in the present specification, the modifying method of the present invention including the deletion method and the replacement method of the present invention is referred to simply as "the present invention" or "the method of the present invention".

Figure 1:
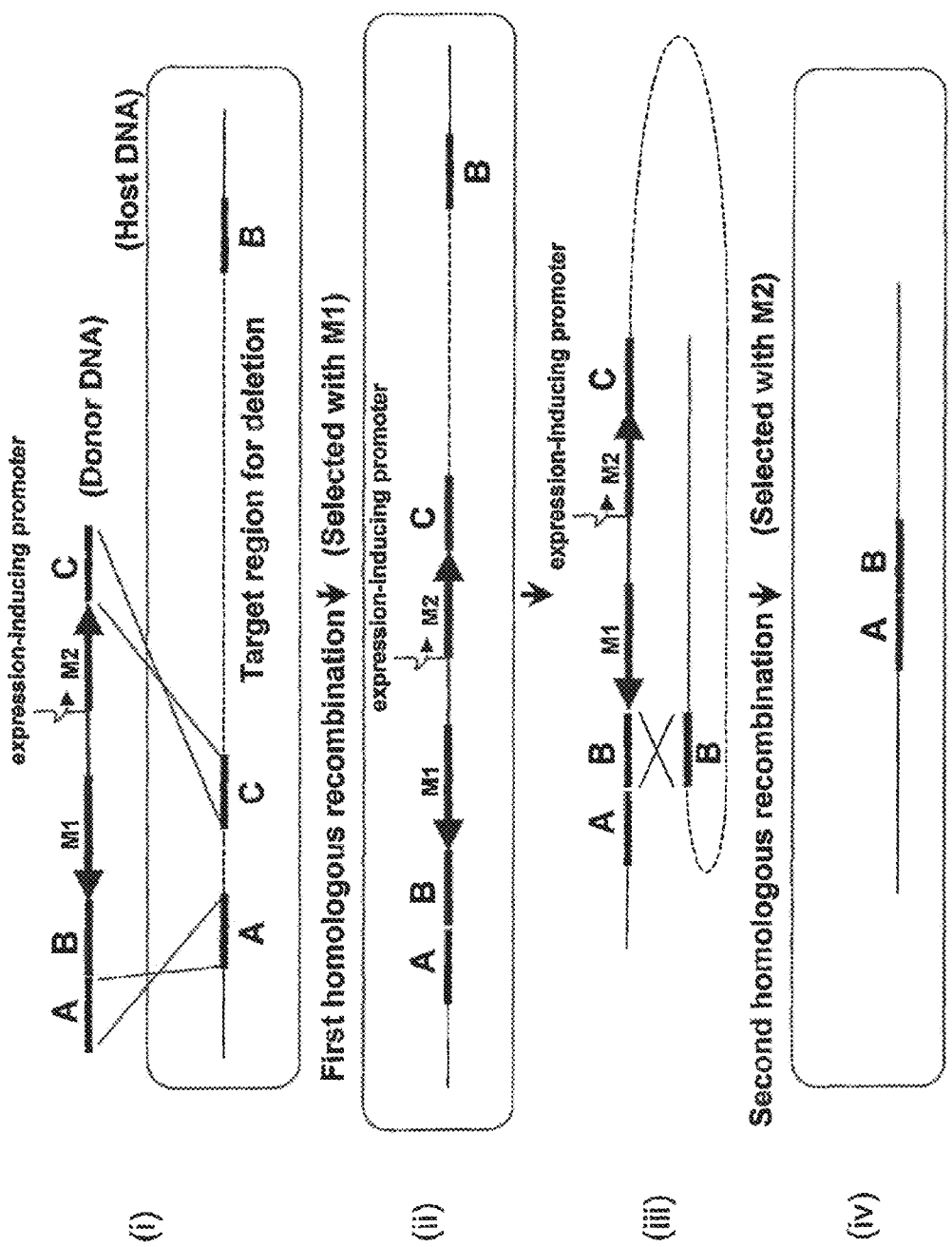
FIG. 1 is a flow diagram showing one embodiment of the method of deleting the target region in the host DNA according to the present invention.

An embodiment of the method of deleting the target region for deletion in the host DNA of the present invention is shown in FIG. 1.

Figure 2:
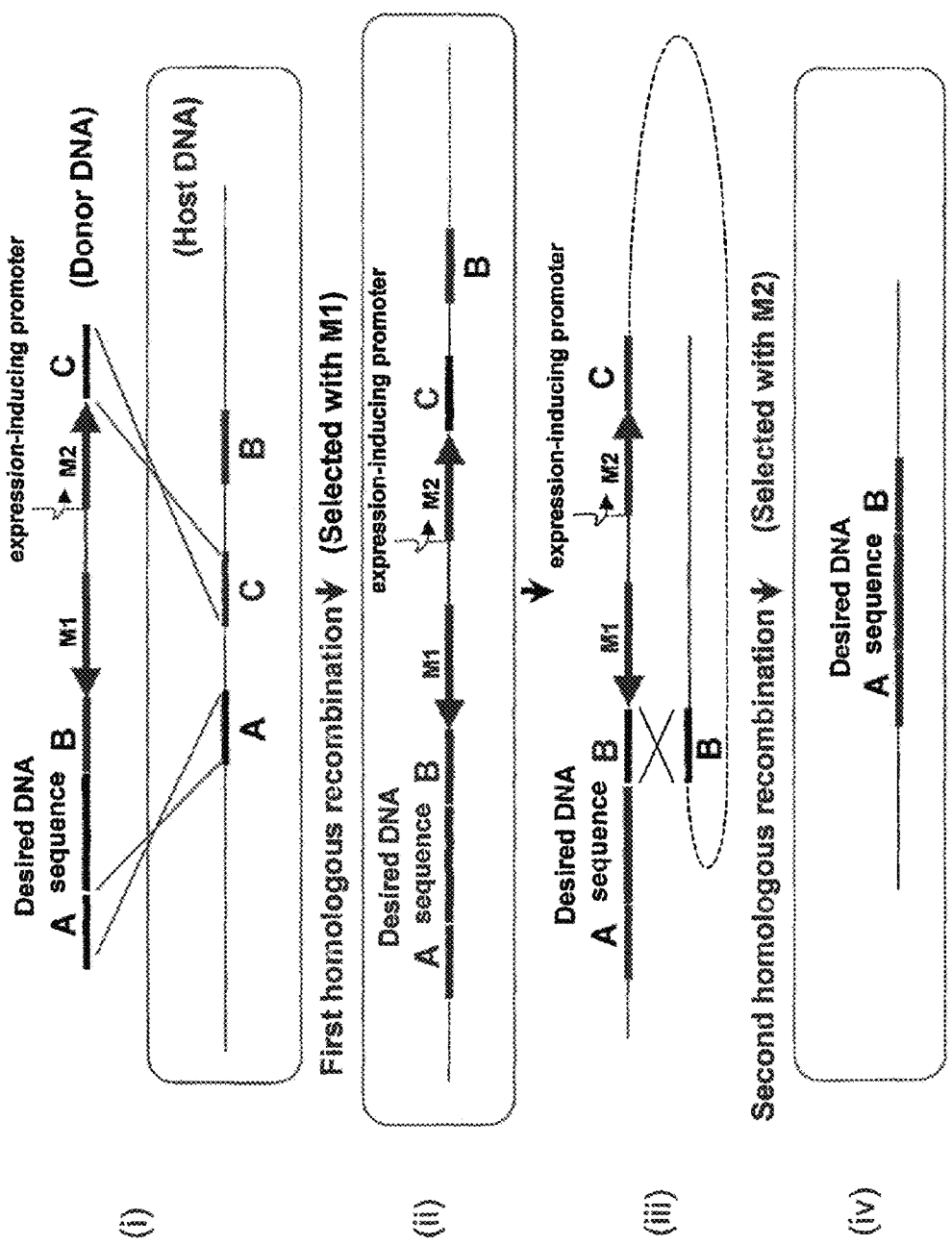
FIG. 2 is a flow diagram showing one embodiment of the method of replacing the target region in the host DNA according to the present invention.

An embodiment of the method of replacing the target region for replacement in the host, DNA of the present invention is shown in FIG. 2. According to the embodiment showing FIG. 2, the DNA sequence of the target region in host DNA can be replaced with the desired DNA sequence and the desired DNA sequence can be inserted into the host DNA.

First, the target region according to the present invention will be explained.

In the present invention, the term "target region in a host DNA" means any region present in the host DNA where the DNA sequence is to be modified. Specifically, in the case of the deletion method of the present invention, the target region is the target region for deletion, that is, the region to be desirably deleted from the host DNA. In the case of the replacement method of the present invention, the target region is the target region for replacement, that is, the region in the host DNA to be desirably replaced with the desired DNA sequence. Hereinafter, the term "target region" in the present specification includes the target region for deletion and the target region for the replacement.

Examples of the target region include an unneeded region of host DNA such as a region unneeded for production of substance in the host (e.g., sporulation-related gene), a region inhibiting growth of the host or production of substances (e.g., phage region), a gene or a gene group duplicated in the host (e.g., two-component regulating gene), or the like.

In the present invention, the target region may be any region if it is presented in the host DNA before application of the method of the present invention. The target region includes may be an inherent region or a region introduced artificially before application of the method of the present invention. Examples of the artificially introduced regions include a region including a selectable marker gene, a region including a reporter gene, and the like.

In the method of the present invention, the size of the target region is not particularly limited, but preferably 1 bp or more, more preferably, 0.2 kb or more, and most preferably 0.5 kb or more. The size of the target region is preferably 200 kb or less, more preferably 160 kb or less, still more preferably 120 kb or less, particularly preferably 80 kb or less, and most preferably 40 kb or less. If the size of the target region is 200 kb or less, it is highly possible that there is no gene essential for growth in the target region. As used herein, the "gene essential for growth" means a gene leading to death of the host cell if it is deleted from the host genome and a gene encoding a protein with a function that cannot be compensated, for example, by exogenously adding the material to the medium. In other words, if the host can proliferates by adding any complementary substance (e.g., metabolism-related substance) to the medium, a gene leading to death of the host cell if it is deleted from the host genome may be contained in the target region. The maximum region containing no gene essential for growth in *Bacillus subtilis* is a region from dltA gene to yycH gene of approximately 200 kb (Proc. Natl. Acad. Sci. USA, 100, 4679 (2003)).

First, in the method of the present invention, the 5'-side region outside of the target region and 3'-side region outside of the target region in the host DNA are identified. In the present invention, each of the 5'-side region outside of the target region and 3'-side region outside of the target region means a region adjacent to the target region, but do not contain the target region. That is, the target region lies between the 5'-side region outside of the target region and 3'-side region outside of the target region. Hereinafter, the 5'-side region outside of the target region will be referred to as "5'-outside-region", and the 3'-side region outside of the target region will be referred to as "3'-outside-region". The nucleotide sequences of the 5'-outside-region and the 3'-outside-region can be identified by using a database containing the nucleotide sequence information of the organism genome, and can also be identified by analyzing the nucleotide sequence of the target region and a neighboring nucleotide sequence thereof. In the present specification, the terms 5' and 3' are to be understood that they are associated with one of the strands of the double-stranded nucleic acid. In FIG. 1 and FIG. 2, the 5'-outside-region is represented by A, while the 3'-outside-region is represented by B.

Next, the first homologous recombination region is identified. The first homologous recombination region is located inside the targeted region in the host DNA. In the present invention, the first homologous recombination region means a region that can perform the first homologous recombination between the Donor DNA and the host DNA together with the 5'-outside-region described above. In FIG. 1 and FIG. 2, the first homologous recombination region is represented by C. The first homologous recombination region C may be located close to the 5'-outside-region, but is preferably a region separated from the 5'-outside-region in the direction toward 3' region by 0 kb to 200 kb, particularly preferable 0 kb to 140 kb.

Similarly to the targeted region described above, the first homologous recombination region may be any region if it is presented in the host DNA before application of the method of the present invention; because the first homologous recombination region is located inside the targeted region. The first homologous recombination region includes may be an inherent region or a region introduced artificially before application of the method of the present invention. Examples of the artificially introduced regions include a region including a selectable marker gene, a region including a reporter gene, and the like.

Figure 3:
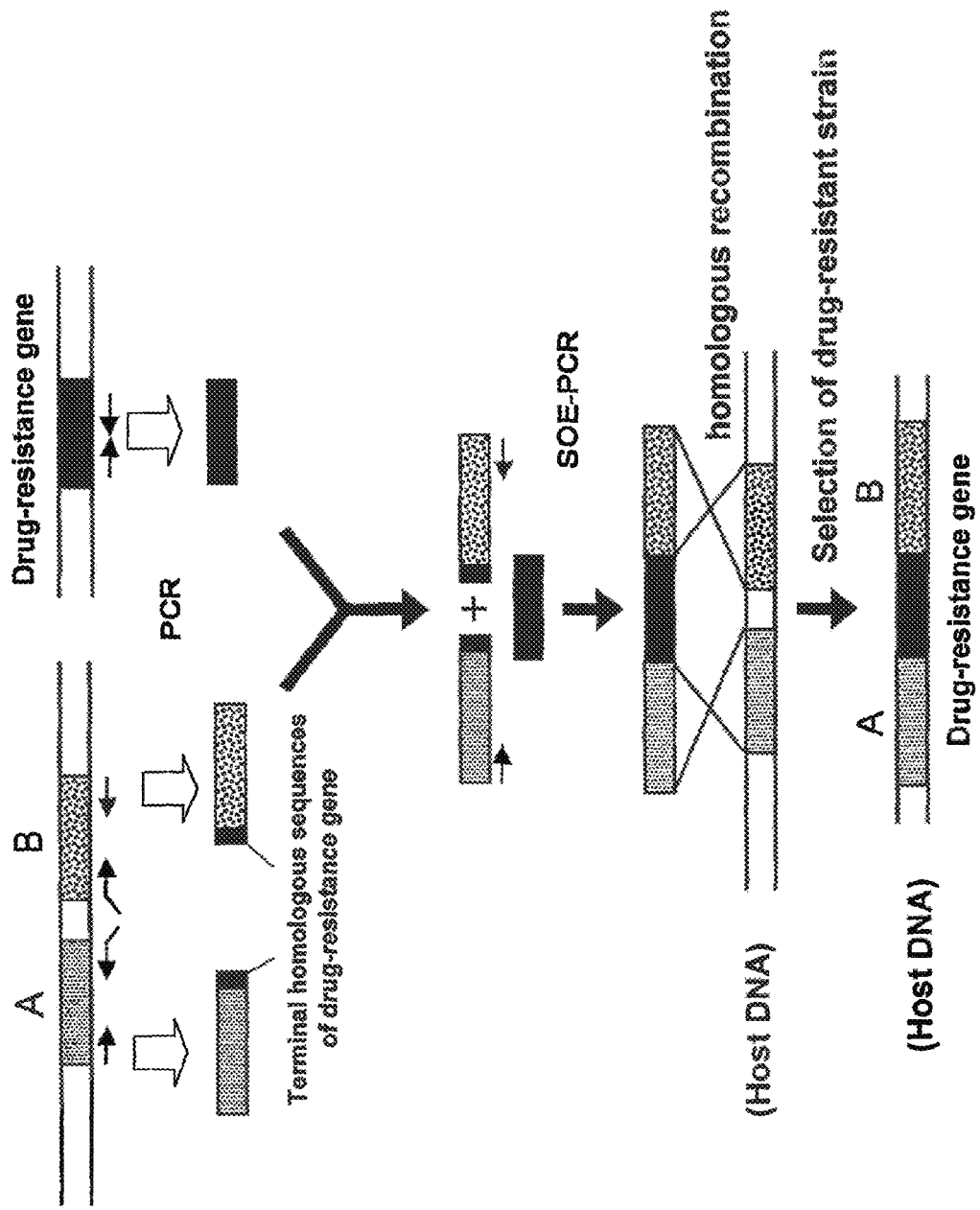
FIG. 3 is a flow diagram showing a process of introducing a drug-resistance gene by a double crossover method using a SOE-PCR fragment.

If there is no first homologous recombination region having sufficient length between the 5'-outside-region and the 3'-outside-region of the host DNA; alternatively, if there is no DNA sequence at all between the 5'-outside-region and the 3'-outside-region, it is possible to form a first homologous recombination region by inserting a known DNA sequence (e.g., a DNA sequence of drug-resistance gene, etc.) into the host DNA by using a common genetic manipulation method. For example, as shown in FIG. 3, a region A derived from host DNA, a region B derived from host DNA, and a drug-resistance gene sequence are constructed by SOE (splicing by overlap extension)-PCR method (see, for example, Horton, R M., at al.: Gene, 77, pp. 61-68 (1989)) and the drug-resistance gene can be introduced into the host DNA by double-crossover homologous recombination between the region A and the region B of the host DNA.

Figure 4:
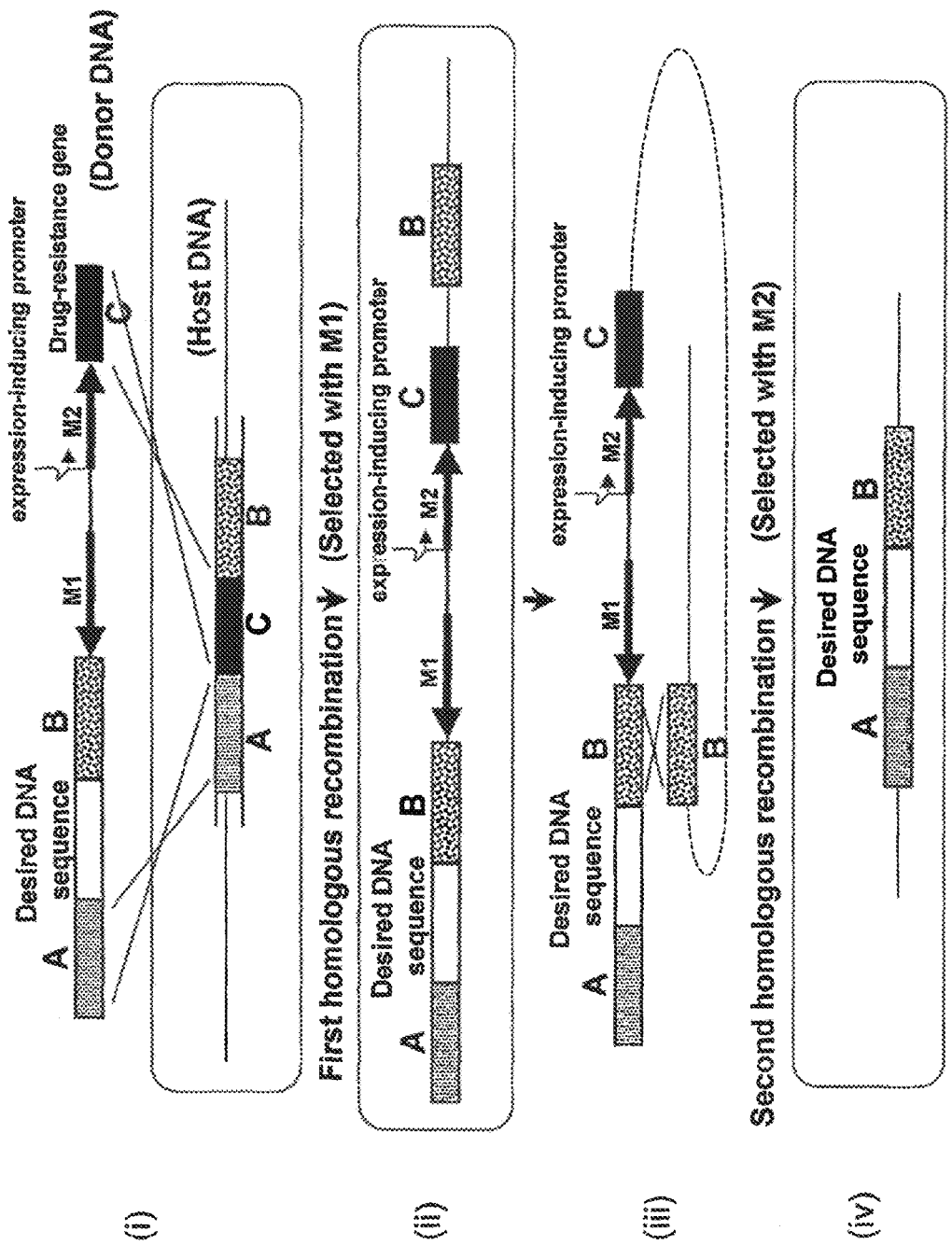
FIG. 4 is a flow diagram showing a process of inserting a desired DNA sequence into a host DNA introduced with a drug-resistance gene, as one embodiment of the method of modifying the target region in the host DNA according to the present invention.

By using a host DNA previously introduced with a DNA sequence such as drug-resistance gene as the first homologous recombination region as described above, it is possible to insert only a desired DNA sequence into the host DNA while the native sequence of the host DNA is retained by the replacement method of the present invention (see FIG. 4). In such a case, the DNA sequence previously inserted as the first homologous recombination region is removed from the host DNA through the second homologous recombination step described later and does not remain in the host DNA after modification (see FIG. 4(*iv*)). The method of the present invention includes such a method of the insertion of a desired DNA sequence into a target region while the host DNA sequence is retained.

After the determination of the 5'-outside-region, the 3'-outside-region and the first homologous recombination region in the host DNA, the donor DNA using the present invention is identified.

In the present invention, the donor DNA can be used for modifying, deleting and replacing the target region (the target region for deletion and the target region for replacement) placed between the 5'-outside-region and the 3'-outside-region in the host DNA. The donor DNA that can be used in the present invention has the region homologous to the 5'-outside-region A of the host DNA, the region homologous to the 3'-outside-region B of the host DNA and the region homologous to the first homologous recombination region C of the host DNA in that order. (Hereinafter, each of these regions is referred to as "homologous region".) In addition to the three homologous regions, the donor DNA has the selectable marker cassette between the homologous regions of the 3'-outside-region B and the first homologous recombination region C (see Donor DNA in FIG. 1(i) and FIG. 2(i)). Hereinafter, these homologous regions of donor DNA will also be simply referred to as 5'-outside-region of donor DNA, 3'-outside-region of donor DNA, and the first homologous recombination region of donor DNA. In FIGS. 1 and 2, the 5'-outside-region of the donor DNA is represented by A; the 3'-outside-region is represented by B; and the first homologous recombination region of the donor DNA is represented by C.

The selectable marker cassette is a nucleotide fragment having the first selectable marker gene M1, the expression-inducing promoter and the second selectable marker gene M2 expressed under the control of the expression-inducing promoter.

In the present invention, the 5'-outside-region of the donor DNA, the 3'-outside-region of the donor DNA and the first homologous recombination region of the donor DNA are involved in genetic exchange between two strands of DNA in the process of homologous recombination between the host DNA and the donor DNA or in the process of homologous recombination in the host DNA after incorporation of the donor DNA into the host DNA. Thus, each of the 5'-outside-region of the donor DNA, the 3'-outside-region of the donor DNA and the first homologous recombination region of the donor DNA has a sufficiently high sequence homology (identity) to perform the homologous recombination between these regions and the corresponding regions of the host DNA.

The nucleotide sequence homology between respective regions is calculated, for example, by Lipman-Pearson method (Science, 227, 1435, (1985)). Specifically, it can be calculated by performing analysis using a homology analysis (Search homology) program of genetic information processing software Genetyx-Win (Software Development) while the unit size to compare (ktup) is set to 2. The calculation results show that the nucleotide sequences of respective regions preferably has an homology of 60% or more, more preferably 80% or more, still more preferably 90% or more, particularly preferably 95% or more, and most preferably 99% or more.

The size of the 5'-outside-region, the 3'-outside-region and the first homologous recombination region in the donor DNA or the host DNA is not particularly limited, if the size is suitable for formation of the interchain exchange structure, and, for example, preferably 0.1 kb to 3 kb, more preferably 0.5 kb to 3 kb, and particularly preferably 0.5 kb to 2 kb.

Next, the selectable marker cassette according to the present invention will be described. The selectable marker cassette according to the present invention has the first selectable marker gene M1, the expression-inducing promoter, and the second selectable marker gene M2 expressed under regulation of the expression-inducing promoter. The selectable marker cassette is located between the 3'-outside-region of the donor DNA and the first homologous recombination region of the donor DNA.

The size of the selectable marker cassette is not particularly limited, but preferably 3 kb to 10 kb, more preferably 3 kb to 5 kb.

The first selectable marker gene M1 that can be used in the present invention is not particularly limited, and examples thereof include a drug-resistance gene (chloramphenicol-resistance gene, erythromycin-resistance gene, neomycin-resistance gene, spectinomycin-resistance gene, kanamycin-resistance gene tetracycline-resistance gene and blasticidin S-resistance gene, etc.). Alternatively, a nutrition requirement-related gene may be used as the first selectable marker gene M1.

In the present invention, the first selectable marker gene M1 is preferably a drug-resistance gene, most preferably a spectinomycin-resistance gene or a kanamycin-resistance gene.

The second selectable marker gene M2 according to the present invention is not particularly limited, as long as it is a gene different from the first selectable marker gene M1 described above and a gene showing a phenotype selectable if it is eliminated from the host DNA.

As the second selectable marker gene M2, for example, a lacZ gene (β-lactamase-coding gene) can be used. When lacZ gene-expressing cells are cultured in a x-gal-containing medium, x-gal is decomposed, and thus, blue colonies can be observed. Accordingly if the lacZ gene is used as the second selectable marker gene M2, the cells lacking the second selectable marker gene M2 form colonies in normal color, thereby selecting desired transformed cells by observing the color of colonies. If lacZ gene-expressing cells are cultured in lactose-containing MacConkey medium, decomposition of lactose can be observed. Therefore, if the lacZ gene is used as the second selectable marker gene M2, cells lacking the second selectable marker gene M2 do not lead to lactose decomposition, thereby selecting cells, lacking the marker gene by observing the concentration of lactose in the medium.

As the second selectable marker gene M2, an amyE gene (amylase-coding gene) can be used. Culture of amyE gene-expressing cells in a starch-containing medium allows observation of halo formation by decomposition of starch components. Thus, if the amyE gene is used as the second selectable marker gene M2, the cell lacking the second selectable marker gene M2 does not lead to decomposition of starch components, thereby selecting desired cells by observing presence of halo formation.

As the second selectable marker gene M2, a gene encoding a protein emitting light by excitation light, such as gfp gene (yfp gene, cfp gene, bfp gene, or rfp gene), can be used. For example, if a gfp gene is used as the second selectable marker gene M2, the cell having the second selectable marker gene M2 allows observation of fluorescence, while the cell lacking the second selectable marker gene M2 does not allow observation of fluorescence. It is thus possible to select the cell lacking the second selectable marker gene M2 by observing the fluorescence of cell.

The second selectable marker gene M2 is preferably is preferably a gene leading to the death of cells (hereinafter, referred to as lethal gene). Examples of the lethal gene include a gene encoding a cell proliferation-inhibiting protein such as chpA gene (ribonuclease-coding gene) or ccdB gene (DNA gyrase inhibitor-coding gene), Kid gene, RelE gene, SymE gene (Endoribonuclease-coding gene), Hok gene, TxpA gene (Lytic peptide-coding gene), Doc gene (Protein synthesis inhibition-related gene), and PerE gene (DNA gyrase inhibition-related gene). Among these, a lethal gene that can be used in the present invention is more preferably the gene encoding a cell proliferation-inhibiting protein such as chpA gene (ribonuclease-coding gene) or ccdB gene (DNA gyrase inhibitor-coding gene). The cell expressing the lethal gene such as chpA gene does not proliferate and dies. If the lethal gene such as chpA gene is used as the second selectable marker gene M2, the cell lacking the second selectable marker gene M2 can proliferate and grow, and thus, it is possible to select the desired transformant by observing colony formation.

The chpA gene is known as a gene encoding mazF toxin, a kind of toxin to *Escherichia coli*. The nucleotide sequence of the chpA gene is shown as SEQ ID No. 1, and the amino acid sequence of the toxin coded by the chpA gene is shown as SEQ ID No. 2.

The second selectable marker gene M2 in the donor DNA or the selectable marker cassette is placed at a position where it is expressed under the control of the expression-inducing promoter. In the present invention, the term "expression-inducing promoter" means a promoter having a function to induce gene expression only under a particular condition. Examples of the particular conditions include presence of an induction substance (inducer), presence of a medium component such as carbon source, temperature, and others.

The expression-inducing promoter that can be used in the present invention is preferably a promoter having a function to induce downstream gene expression in the presence of an induction substance (inducer).

Examples of the expression-inducing promoters include, but are not limited to, a lac promoter and a spac promoter inducing expression in the presence of isopropyl-β-D-thiogalactopyranoside (IPTG), a xylose-inducible promoter, an arabinose-inducible promoter, a ECF sigma factor-specific promoter (see, for example, *Bacillus subtilis* and its closest relatives. pp. 289-312, RNA polimerase and Sigma factors, J. Helmann and C. Moran Jr., Editors: A. Sonenshein, J Hoch, R Losick: ASM Press), a promoter regulated by Mg/Cu two-component regulation system, and the like. Among there, a spac promoter is preferably used in the present invention.

If the lac promoter or spec promoter is used, the donor DNA or the selectable marker cassette contains a lacI gene encoding the repressor inhibiting these promoters in the absence of IPTG. The repressor-coding gene, lacI gene, is also placed between the 3'-outside-region B and the first homologous recombination region C of the donor DNA.

The donor DNA, including the 5'-outside-region A, the 3'-outside-region B, the first selectable marker gene M1, the expression-inducing promoter, the second selectable marker gene M2 and the first homologous recombination region C, can be prepared by using the conventional gene manipulation techniques. For preparing the donor DNA, for example, a DNA fragment such as a PCR product, entire genome or a part of it, a plasmid, a shuttle vector, a helper plasmid, a phage DNA, a virus vector, a BAC DNA (Proc. Natl. Acad. Sci. USA 87, 8242 (1990)) and a YAC DNA (Science 236, 806 (1987)) and the like can be used. Further, a DNA fragment, a part of genome DNA and the like cloned in a plasmid; a shuttle vector, a helper plasmid, a phage DNA, a virus vector, a BAC and YAC DNAs, and the like can be used.

Examples of the plasmid include a *Escherichia coli*-derived plasmid (e.g., pET plasmids such as pET30b, pBR plasmids such as pBR322 and pBR325, pUC plasmids such as pUC118, pUC119, pUC18 and pUC19, a pBluescript plasmid, etc.), a *Bacillus subtilis*-derived plasmid (e.g., pUB110, pTP5, etc.), a yeast-derived plasmid (e.g., YEp plasmids such as YEp13, YCp plasmids such as YCp50, etc.) and the like. Examples of the phage DNA include a λphage (e.g., Charon4A, Charon21A, EMBL3, EMBL4, λgt10, λgt11, λZAP, etc.) and a PBS1 phage (see, for example, J. Bacteriol. 90, 1575 (1965)). Further, an animal virus vector such as retrovirus or vaccinia virus, a plant virus vector such as cauliflower mosaic virus, and an insect virus vector such as baculovirus can be used. Alternatively, if LP (lysis of protoplasts) transformation method (see, for example, T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) is used, for example, a microorganism having a donor DNA itself such as *Bacillus subtilis* may be used.

The donor DNA used in the replacement method of the present invention will be described below more in detail.

The donor DNA used in the replacement method of the present invention has the desired DNA sequence between 5'-outside-region of the donor DNA and the 3'-outside-region of the donor DNA, in addition to the configuration of the donor DNA described above (see FIG. 2(i): donor DNA).

In the present invention, the "desired DNA sequence (hereinafter, also referred to as "DNA sequence of interest")" may be any DNA sequence, if it can be inserted into the target region of host DNA. Examples thereof include a gene encoding a protein, a gene encoding a regulator such as promoter, and the like. The desired DNA sequence may contain a plurality of these genes. For example, the desired DNA sequence may have a promoter sequence and a protein-coding gene sequence, or a plurality of regulator sequences and a plurality of gene sequences.

In the replacement method of the present invention, the size of the desired DNA sequence inserted is not particularly limited, if the donor DNA can be introduced into the host cell, but preferably 1 bp or more and 10 kb or less, more preferably 1 bp or more and 5 kb or less.

The method of preparing the desired DNA sequence that can be used in the present invention is not particularly limited, and the desired DNA sequence may be designed and prepared by the known method such as a PCR method and a method using a DNA ligase. For example, a DNA sequence in combination of any promoter sequence and any gene sequence may be prepared as the desired DNA sequence and then inserted into a desired region of host DNA.

The desired DNA sequence or the donor DNA is not always a PCR product. For example, an desired DNA sequence digested with a restriction enzyme may be ligated into a region between the 5'-outside-region and 3'-outside-region of donor DNA by using a DNA ligase, and the obtained DNA fragment (5'-outside-region-desired DNA sequence-3'-outside-region) may be amplified by PCR method, and then, the amplified product and a selectable marker cassette may be connected to each other by using a DNA ligase, to prepare a donor DNA.

According to the replacement method of the present invention, it is possible to insert the desired DNA sequence into the host by replacing the target region in the host DNA with the desired DNA sequence. By using the replacement method of the present invention, it is possible to insert a DNA fragment that is hard to clone by a conventional method of using a plasmid (e.g., large-sized DNA sequence, membrane protein-coding gene, gene showing toxicity when introduced in host cell and resistant to insertion into a multi-copy plasmid, or DNA sequence containing a plurality of gene groups, a plurality of regulators and others) into the host DNA with simple and easy procedure. It is also possible by the replacement method of the present invention to insert a plurality of large-sized DNA fragments into a plurality of sites (loci) in the host DNA.

It is thus possible by the replacement method of the present invention to insert a gene group such as gene group encoding proteins forming a biosynthetic system and gene group encoding proteins functioning as a protein complex as they are expressed, in the same cell. As a result, it is possible to perform functional analysis of the gene group in cell by expressing the inserted genes of the gene group simultaneously in the cell. In metagenome analysis in recent years, DNAs recovered from environmental samples are cloned into a plasmid for sequencing. The DNAs present in an environment contains many DNA fragments that can not be cloned into plasmid. The replacement method of the present invention is also useful for cloning such DNA fragments and functional analysis of the genes in the DNA fragments.

In the present invention, the donor DNA is constructed by the above described procedure and is introduced into the host DNA for the modification, deletion or replacement of the target region in the host DNA.

The host DNA according to the present invention includes a genome DNA, a mitochondrial DNA and the like in an organism.

Examples of the host (recipient) according to the present invention include *Bacillus* species such as *Bacillus subtilis*, *Escherichia* species such as *Escherichia coli*, and *Pseudomonas* species such as *Pseudomonas putida*; yeasts such as *Saccharomyces cerevisiae* and *Schizosaccharomyces pombe*; animal cells such as simian cell COS-7, Vero, Chinese hamster oval cell (CHO cell) and mouse L cell; insect cells such as Sf9; plants such as Poaceae (rice (*Oryza sativa*), corn (*Zea mays*)), Brassicaceae (Thale Cress (*Arabidopsis thaliana*)), Solanaceae (tobacco (*Nicotiana tabacum*) and Fabaceae (soybean (*Glycine max*)); and the like. In particular, *Bacillus subtilis* is preferably used as the host according to the present invention.

In the present invention, the method of introducing the donor DNA into the host is not particularly limited, if it is a method of introducing DNA into cell. For example, a method of using calcium ion, electroporation method, and the like may be used.

When *Bacillus subtilis* is used as the host, competent cell transformation method (see, for example, J. Bacterial. 93, 1925 (1967)) or LP transformation method (see, for example, T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) may be used.

When yeast is used as the host, the method of introducing DNA is not particularly limited, if it can introduce DNA into yeast. For example, an electroporation method, spheroplast method, lithium acetate method and the like may be used.

When an animal cell is used as the host, examples of the method of introducing DNA into animal cell include an electroporation method, calcium phosphate method, lipofection method and the like. When an insect cell is used as the host, examples of the method of introducing DNA into insect cell include a calcium phosphate method, lipofection method, electroporation method and the like. When a plant is used as the host, examples of the method of introducing DNA into plant cell include an electroporation method, *agrobacterium* method, particle gun method, PEG method and the like.

In the present invention, after introduction of the donor DNA into the host by the method described above, the donor DNA and the host DNA are brought close to each other under the condition of homologous recombination, thereby causing double-crossover homologous recombination between the donor DNA and the host DNA at the regions of the 5'-outside-region A and the first homologous recombination region C (in FIGS. 1 and 2, "first homologous recombination"). As the result of the double-crossover homologous recombination (the first homologous recombination), in the deletion method of the present invention, the 3'-outside-region B of the donor DNA, the first selectable marker gene M1 and the second selectable marker gene M2 can be introduced to the position between the 5'-outside-region A of the host DNA and the first homologous recombination region C of the host DNA (see FIG. 1(*ii*)). In the replacement method of the present invention, the desired DNA sequence of the donor DNA, the 3'-outside-region B of the donor DNA, the first selectable marker gene M1 and the second selectable marker gene M2 can be introduced into the position between the 5'-outside-region A of the host DNA and the first homologous recombination region C of the host DNA (see FIG. 2(*ii*)).

The term "condition of homologous recombination" means a condition in which the inherent functions of the host such as a function of recombination reaction-related enzymes are not lost.

Examples of the methods of carrying out the recombination between the donor DNA and host DNA include general competent cell transformation method (see, for example, J. Bacterial. 93, 1925 (1967)), protoplast transformation method (see, for example, Mol. Gen. Genet. 168, 111 (1979)), electroporation method (see, for example, FEMS Microbiol. Left 55, 135 (1990)), and LP transformation method (see, for example, T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829).

If the host is *Bacillus subtilis*, for example, the transformation can be performed according to the competent cell transformation method (see, for example, J. Bacterial. 93, 1925 (1967)) in the following manner.

The host cells are shake-cultured in SPI medium (0.20% (W/V) ammonium sulfate, 1.40% (W/V) dipotassium hydrogen phosphate, 0.60% (W/V) potassium dihydrogen phosphate, 0.10% (W/V) trisodium citrate dihydrate, 0.50% (W/V) glucose, 0.02% (W/V) casamino acid (Difco), 5 mM magnesium sulfate, 0.25 µM manganese chloride, and 50 µg/ml tryptophan) at 37° C., for example to growth rate (O.D. 600) of about 1. After the shake culture, part of the culture solution is inoculated in a 9-time volume of SPII medium (0.20% ammonium sulfate, 1.40% (W/V) dipotassium hydrogen phosphate, 0.60% (W/V) potassium dihydrogen phosphate, 0.10% (W/V) trisodium citrate dihydrate, 0.50% (W/V) glucose, 0.01% (W/V) casamino acid (Difco), 5 mM magnesium sulfate, 0.40 µM manganese chloride, 5 µg/ml tryptophan), and the mixture was shake-cultured, for example to growth rate (O.D. 600) of about 0.4, to prepare competent cells of the host cells.

Then, the donor DNA is added to the competent cells of the host strain. The amount of the donor DNA added is not particularly limited, but preferably 100 µg to 100 µg, and more preferably 1 ng to 10 µg. The competent cells are preferably used at $10^5$ to $10^9$ CFU, and more preferably $10^6$ to $10^8$ CFU. The donor DNA is added to the competent cells of the host strain, and the cells are cultured for 1 hour to 2 hours.

In the steps above, the donor DNA is introduced into the host cell, thereby causing the first homologous recombination between the donor DNA and the host DNA (see FIG. 1(*i*) to (ii) and FIG. 2(*i*) to (ii), "First homologous recombination").

After the first homologous recombination, recombinant hosts can be selected based on expression of the first selectable marker gene derived from the donor DNA. Because the first selectable marker gene is expressed in the recombinant host after the first homologous recombination, it is possible to select the recombinant hosts after the first homologous recombination from the other hosts by observing the phenotype of the marker gene. For example, when a drug-resistance gene described above is used as the first selectable marker gene, host cells with the drug resistance may be selected.

After single colony isolation, the recombinant hosts (e.g., transformants of *Bacillus subtilis*) obtained by the first homologous recombination are cultured for 0 to 48 hours (preferably 1 to 24 hours, particularly preferably 2 to 3 hours), to perform homologous recombination between the two 3'-outside-regions in the host DNA (second homologous recombination; see FIG. 1(*iii*) and FIG. 2(*iii*)). The second homologous recombination leads to the modification of the target region in the host DNA and the deletion of the first selectable marker gene and the second selectable marker gene from the host DNA (see FIG. 1(*iv*) and FIG. 2(*iv*)). Because of the deletion of the first selectable marker gene, a phenotype of transformant obtained after the second homologous recombination has been changed. when a drug-resistance gene is used as the first selectable marker gene, the drug resistance obtained by the first homologous recombination is lost and thus, the transformant shows a drug-sensitive phenotype.

After the second homologous recombination, the second selectable marker gene expressed under the control of the expression-inducing promoter is also deleted from the host DNA. Accordingly, no second selectable marker gene is expressed in the host which is modified by the second homologous recombination, even if the host cells are cultured under expression-inducing condition.

If the second homologous recombination is unsuccessful, the expression-inducing promoter and the second selectable marker gene remain in the host DNA. In this case, the second selectable marker gene is expressed in the host under expression-inducing condition.

In this way, it is possible to select the host with second homologous recombination from the other hosts based on expression of the second selectable marker gene.

When lacZ gene is used as the second selectable marker gene, it is possible to select the hosts with second homologous recombination from other hosts based on the blue color development by x-gal decomposition on x-gal-containing medium. Specifically, the hosts with second homologous recombination give colonies in normal color, because the lacZ gene is not expressed. It is thus possible to select only the hosts with second homologous recombination by selecting non-blue normal colored colonies.

When amyE gene is used as the second selectable marker gene, it is possible to select the hosts with second homologous recombination from other hosts based on the halo formation on starch-containing medium. Thus, the hosts with second homologous recombination do not form halo because the amyE gene is not expressed. It is thus possible to select only the hosts with second homologous recombination by selecting hosts giving normal colonies without halo formation.

When gfp gene is used as the second selectable marker gene, it is possible to select the hosts with second homologous recombination from other hosts based on fluorescence. Specifically, the hosts with second homologous recombination do not show fluorescence, because the gfp gene is not expressed. It is thus possible to select only the hosts with second homologous recombination from other hosts by selecting hosts giving colonies with no observed fluorescence.

In the present invention, the second selectable marker gene is preferably a selectable marker gene which allows the selection of the transformant after the second homologous recombination by positive selection. It is possible by using such a selectable marker gene to select only the transformant which is modified by the second homologous recombination, at high accuracy without selection of pseudopositive clones.

In the present invention, the term "positive selection" means a method of selecting a desired transformant based on the proliferation potency only of the desired transformant in a particular medium.

In the present invention, the term "negative selection" means a method of selecting a desired transformant based on the defect in the proliferation potency only of the desired transformant in a particular medium, or a method of selecting a desired transformant based on the defect in production potency of a particular protein. As used herein, the "defect in proliferation potency in a particular medium" means, for example, that the desired transformant loses its potency to produce a particular protein and does not proliferate or remain alive in the particular medium.

In the present invention, the second selectable marker gene which allows selection of a desired transformant by positive selection is preferably the lethal gene described above such as chpA gene, ccdB gene, Kid gene, RelE gene, SymE gene, Hok gene, TxpA gene, Doc gene, PerE gene and the like.

If the lethal gene is used as the second selectable marker gene, only the host lacking the second selectable marker gene through the second homologous recombination can proliferate and grow in normal medium. While the host which fails to the second homologous recombination can not proliferate and dies due to of the expression of the lethal gene. Using the above lethal gene as the second selectable marker gene, it is possible to select the desired transformant with second homologous recombination by positive selection at high accuracy.

On the other hand, if the transformants with the second homologous recombination are to be selected by negative selection, pseudopositive individuals may be erroneously selected as the desired transformants. For example, if the first selectable marker gene used in the first homologous recombination is used also as the selectable marker in the second homologous recombination, individuals with the first homologous recombination are chosen by positive selection, while individuals with the second homologous recombination are to be chosen by negative selection.

In the present invention, two kinds of selectable marker genes (i.e., first and second selectable marker genes) are used, and the second selectable marker gene expression is controlled by the expression-inducing promoter. By selecting the kinds of these selectable marker genes appropriately, it is possible to select the transformant after first homologous recombination by positive selection and the transformant after second homologous recombination by positive selection. The first and second positive selection leads to select the desired transformant at extremely high accuracy without erroneously selecting pseudopositive clones.

For example, the desired transformant with the second homologous recombination can be selected from the other hosts by adding IPTG to the medium when a promoter inducing gene expression in the presence of IPTG such as spac promoter is used as the expression-inducing promoter. In this case, only the desired transformant with the second homologous recombination can grow in the medium containing IPTG, while the other hosts are killed by the lethal gene expression induced by IPTG.

In the above selection using IPTG, it is preferable to repeat doubling of the cell concentration in a liquid medium (such as LB medium) about 6 to 10 times, inoculate the culture on an agar flat plate medium containing 100 µM or more of IPTG and thus, obtain the colony-forming clones, because it suppose that the second homologous recombination occurs simultaneously with chromosomal duplication. Further, for preventing pseudopositive clones caused by the spac promoter mutation due to selection pressure, it is preferable to examine the change in phenotype resulting from deletion of the first selectable marker gene, simultaneously. Specifically, when the spectinomycin-resistance gene is used as the first selectable marker gene, it is preferable to select clones not growing on the agar plate containing 100 µg/ml spectinomycin for confirming their spectinomycin sensitivity. By using the change in phenotype resulting from the deletion of the first selectable marker gene as an additional indicator, it is possible to obtain desired transformant at very high accuracy (almost at 100%).

EXAMPLES

Hereinafter, the present invention will be described more in detail with reference to Examples, but it should be understood that the technological scope of the present invention is not particularly limited by the following Examples.

Example 1

Figure 5:
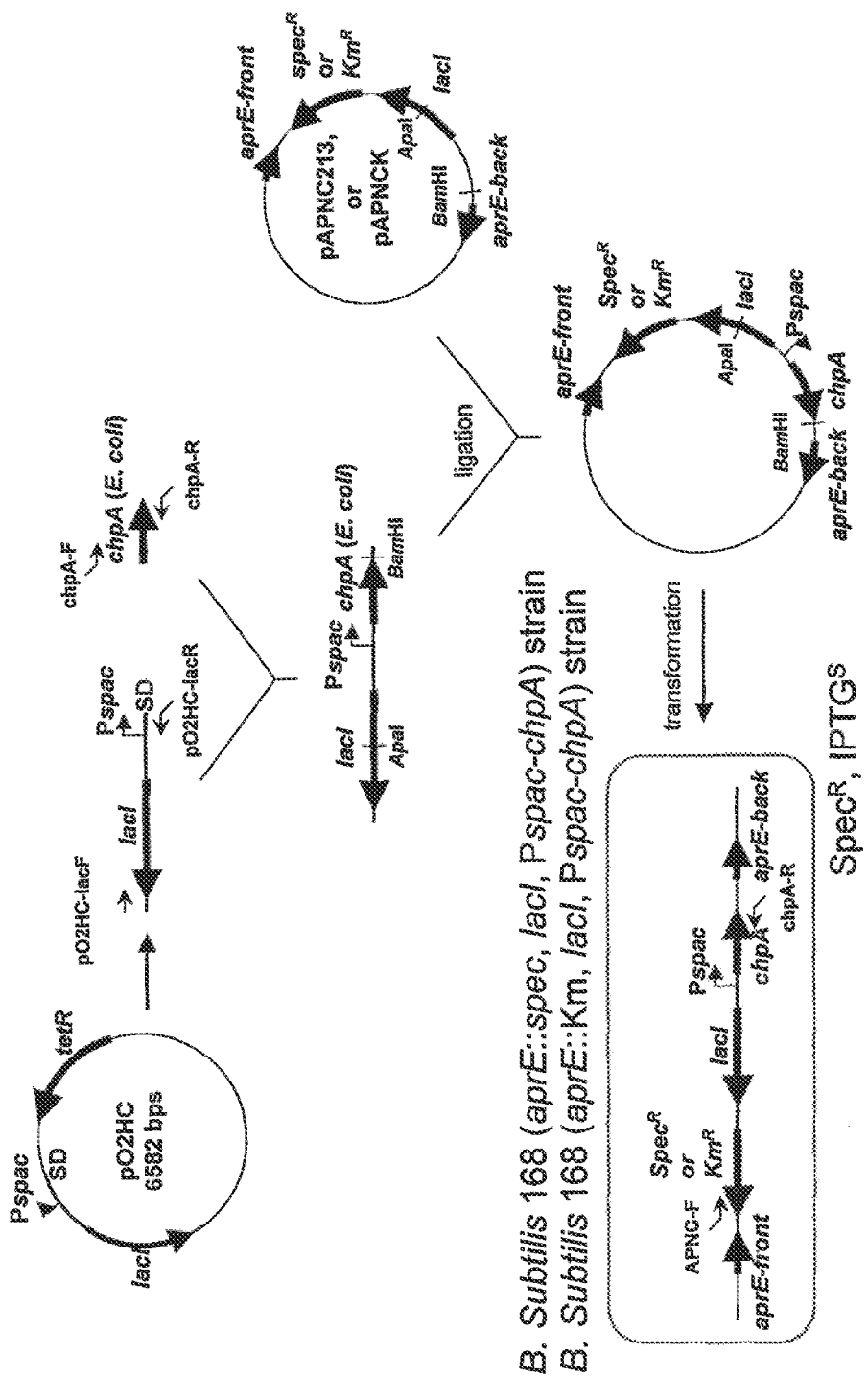
FIG. 5 is a flow diagram showing a process in preparing *Bacillus subtilis* 168 (aprE::spec, lacI, Pspac-chpA) and *Bacillus subtilis* 168' (aprE::km, lacI, Pspac-chpA) used in Example 1 and 2.
Figure 6:
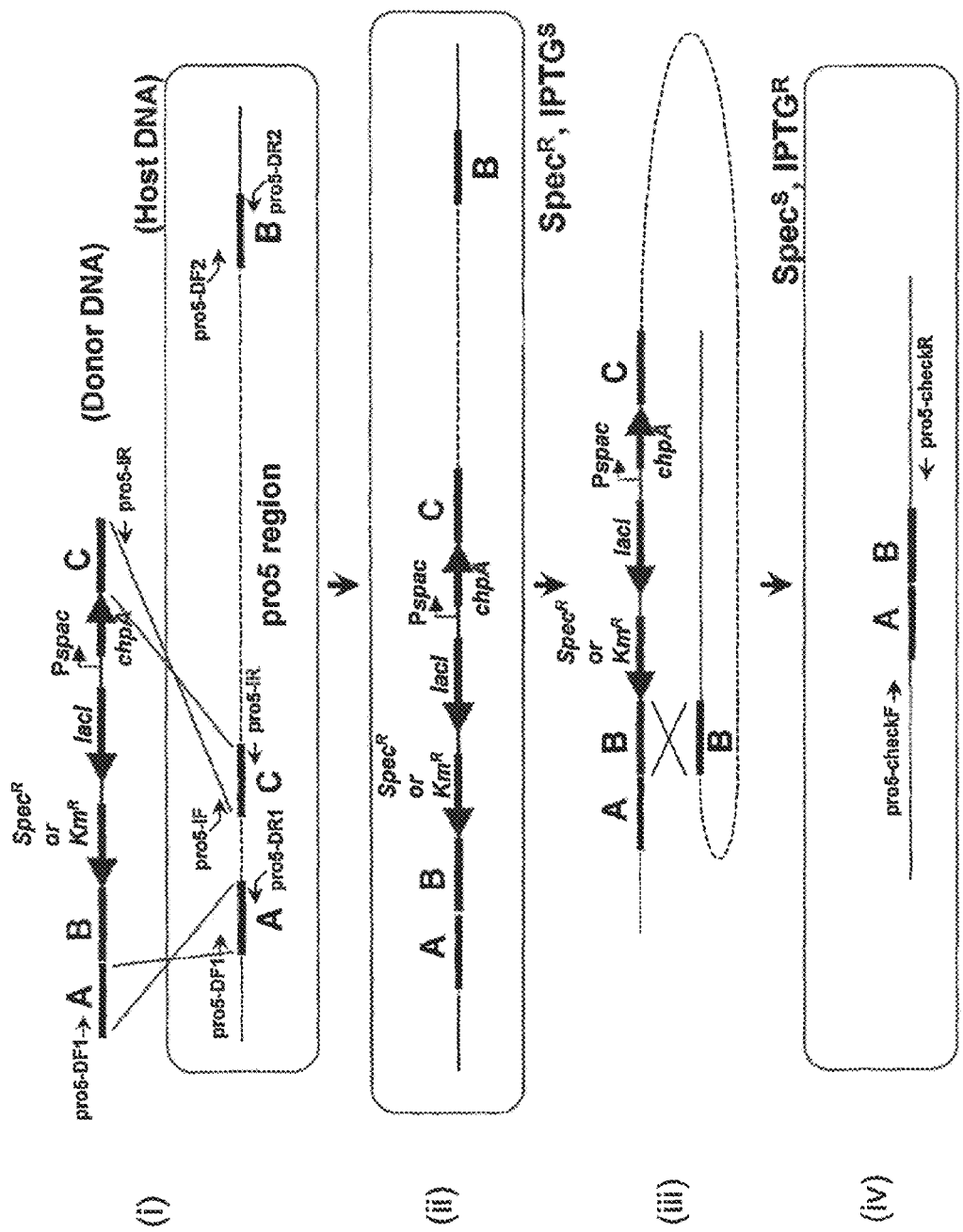
FIG. 6 is a flow diagram showing a process of deleting a target region from a host DNA in Example 1.

In the present Example, the pro5 region (20,485 bp), which is the region from 1,879,258 bp to 1,899,742 bp on the genome of *Bacillus subtilis* 168, was deleted as the target region for deletion. The sequences of the primers used in the present Example are shown in Table 1. The flow diagrams of the present Example are shown in FIG. 5 and FIG. 6.

TABLE 1

Primer sequences

| Primer | Nucleotide sequence | SEQ ID NO: |
|---|---|---|
| pO2HC-lacF | CTCACATTAATTGCGTTGCG | 3 |
| pO2HC-lacR | CTTACCATAGTTAATTTCTCCTCTTTAATG | 4 |
| chpA-F | GAAATTAACTATGGTAAGCCGATACGTACC | 5 |
| chpA-R | CGCGGATCCTACCCAATCAGTACGTTAATTTTG | 6 |
| APNC-F | CGACAGCGGAATTGACTCAAGC | 7 |
| pro5-DF1 | GAGCAAAGAAGAGCGCATGG | 8 |
| pro5-DR1 | CAGCATGGAGAAGATTTCAACGTAATTATGG | 9 |
| pro5-DF2 | CGTTGAAATCTTCTCCATGCTGTGTGATTGATC | 10 |
| pro5-DR2 | CTGATTGGGTAGGATCCGCGATATTTATCGACGAACTCAGAT | 11 |
| pro5-IF | GAGTCAATTCCGCTGTCGATCAATCACAATGGAGGAC | 12 |
| pro5-IR | TACGTAAGTATCAGCACAGG | 13 |
| pro5-checkF | CTGCAAACCCATACCTTGCAC | 14 |
| pro5-checkR | CATCACTAAATCTCTTAAACGTC | 15 |

<Preparation of Donor DNA>

First, mutant strains, *Bacillus subtilis* 168 (aprE::spec, lacI, Pspac-chpA) and *Bacillus subtilis* 168 (aprE::Km, lacI, Pspac-chpA), were constructed in the following manner from *Bacillus subtilis* 168 strain by inserted a DNA fragment containing the spectinomycin-resistance gene or the kanamycin-resistance gene, the lacI gene and the Pspac-chpA gene into the aprE locus of *Bacillus subtilis* 168.

As shown in FIG. 5, the region from the lacI gene to the SD sequence downstream of the spac promoter in *Bacillus subtilis* expression vector pO2HC was amplified by PCR using the vector as a template and using a primer set of pO2HC-lacF (SEQ ID NO: 3) and pO2HC-lacR (SEQ ID NO: 4). An other region from the initiation codon to the termination codon of chpA gene in the genome of *E. coli* W3110 was also amplified by PCR using the genome of *E. coli* W3110 as a template and a primer set of chpA-F (SEQ ID NO: 5) and chpA-R (SEQ ID NO: 6). The two amplified DNA fragments were ligated by SOE-PCR method (Gene, 77, 61 (1989)), to give a ligated DNA fragment.

Then, the ligated DNA fragment was digested with restriction enzymes ApaI and BamHI, to obtain restriction enzyme-digested fragments. Similarly, pAPNC213 (including the spectinomycin-resistance gene: spec$^R$) or pAPNCK (including the kanamycin-resistance gene: Km$^R$) was digested with the restriction enzymes ApaI and BamHI, to obtain restriction enzyme-digested fragments. These restriction enzyme-digested fragments were ligated by using DNA ligase, to obtain a circular DNA.

*Bacillus subtilis* 168 was transformed with the circular DNA, and then plated on LB medium plate containing 100 µg/ml of spectinomycin or 5 µg/ml of kanamycin to select desired transformants. The desired transformants were designated as 168 (aprE::spec, lacI, Pspac-chpA) and 168 (aprE::Km, lacI, Pspac-chpA).

By using the chromosomal DNA of the strain 168 (aprE::spec, lacI, Pspac-chpA) or 168 (aprE::Km, lacI, Pspac-chpA) as a template, a DNA fragment was amplified by PCR using APNC-F primer (SEQ ID NO: 7) and chpA-R primer (SEQ ID NO: 6) (see FIG. 5). The amplified DNA fragment was referred to as selectable marker gene cassette.

In addition, the 5'-outside-region (fragment A) of the target region for deletion, 3'-outside-region (fragment B) of the target region for deletion and the first homologous recombination region (fragment C) were amplified by PCR from the chromosomal DNA of *Bacillus subtilis* 168 using primer sets of pro5-DF1 (SEQ ID NO: 8) and pro5-DR1 (SEQ ID NO: 9), pro5-DF2 (SEQ ID NO: 10) and pro5-DR2 (SEQ ID NO: 11), and pro5-IF (SEQ ID NO: 12) and pro5-IR (SEQ ID NO: 13), respectively (see FIG. 6(i)).

Using the thus-obtained PCR fragments, i.e. the selectable marker gene cassette, the 5'-outside-region (fragment A), the 3'-outside-region (fragment B) and the first homologous recombination region (fragment C), SOE-PCR (Gene, 77, 61 (1989)) were performed with the primer set of pro5-DF1 (SEQ ID NO: 8) and pro5-IR (SEQ ID NO: 13). As a result, a DNA fragment which has the 5'-outside-region (fragment A), the 3'-outside-region (fragment B), the selected marker gene cassette and the first homologous recombination region (fragment C) aligned in that order, was obtained as shown in FIG. 6(i): This DNA fragment was used in the following transformation as a donor DNA.

<Transformation>

1. First Homologous Recombination

Using the PCR product (the donor DNA obtained above) in an amount of 20 μg or more, *Bacillus subtilis* 168 was transformed according to the competent cell transformation method (J. Bacterial. 93, 1925 (1967)). 1 μg of the PCR product (donor DNA) is added to 400 μl of competent cells of *Bacillus subtilis* 168, and the mixture was cultured for 1.5 hours (the first homologous recombination (see FIG. 6(i) to (ii)).

After the transformation (first homologous recombination), the transformants were selected based on expression of the spectinomycin-resistance gene or kanamycin-resistance gene. Specifically, the cells after the transformation were plated on a LB medium plate containing 100 μg/ml of spectinomycin or 5 μg/ml of kanamycin overnight at 37° C., and then colonies grown on the LB medium plate were collected as transformants. Only the mutant *Bacillus subtilis* strain having spectinomycin-resistance or the kanamycin-resistance resulting from the integration of the donor DNA into *Bacillus subtilis* 168 strain through the first homologous recombination, can grow and form colonies on the LB medium plate containing spectinomycin or kanamycin.

2. Second Homologous Recombination

The transformant having the spectinomycin resistance or the kanamycin resistance was cultured overnight in LB liquid medium. After dilution of the culture, the culture solution was applied on a LB medium plate supplemented with 1 mM IPTG. As a result, 48 colonies were obtained. These colonies growing on IPTG-containing LB medium plate are the *Bacillus subtilis* transformants in which the target region for deletion and the donor DNA were both deleted from the host DNA by the second homologous recombination (see FIG. 6(iii) to (iv)).

Further, for confirming the deletion of the pro5 region (the target region for deletion), the obtained 48 single colonies of *Bacillus subtilis* transformants were examined by PCR using pro5-checkF primer (SEQ ID NO: 14) and pro5-checkR primer (SEQ ID NO: 15). As a result, alt 48 transformants did not have the pro5 region.

As is apparent from the above results, it is possible to delete a desired region in *Bacillus subtilis* genome at high accuracy by the method of the present invention using the donor DNA and the selectable marker cassette contained therein.

Further, neither the spectinomycin-resistance gene nor the kanamycin-resistance gene used in the transformation steps as the selectable marker gene remains in the resultant transformant. Therefore, the transformant obtained by the method of the present invention can be repeatedly used for further transformation with the spectinomycin-resistance gene or the kanamycin-resistance gene as the selectable marker gene.

Example 2

Figure 7:
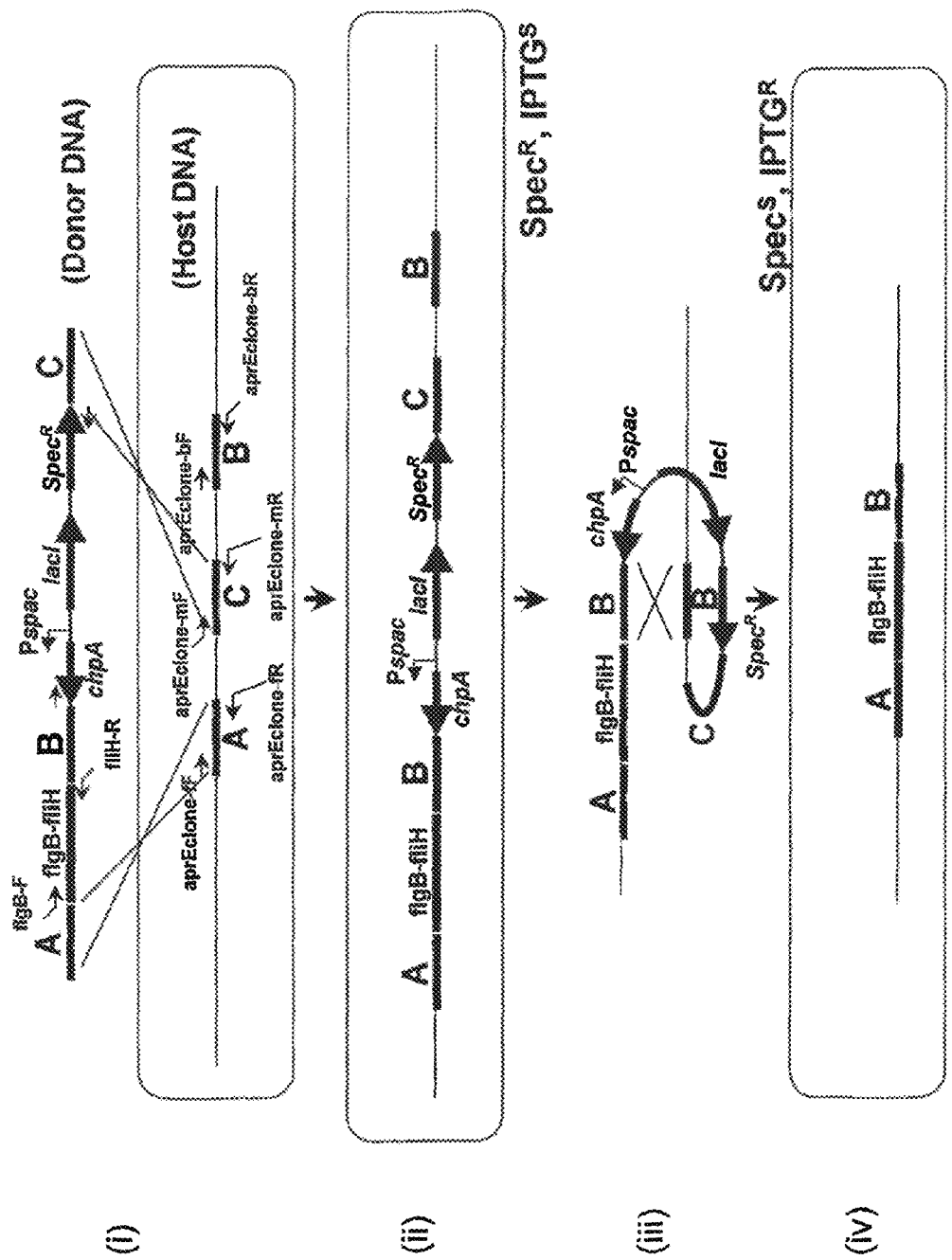
FIG. 7 is a flow diagram showing a process of inserting a DNA sequence into a host DNA in Example 2.

In the present Example, the flgB-fliH region (4,708 bp) corresponding to 1,690,526 bp to 1,695,233 bp in the genome of *Bacillus subtilis* 168 was used as the desired DNA sequence, and the DNA sequence was inserted into the target region for replacement in the host DNA. The sequences of the primers used in the present Example are shown in Table 2. The flow diagram of the present Example is shown in FIG. 7.

TABLE 2

Primer sequences

| Primer | Nucleotide sequence | SEQ ID NO: |
|---|---|---|
| chpA-R | CGCGGATCCTACCGAATCAGTACGTTAATTTTG | 6 |
| APNC-F | CGACAGGGGAATTGACTCAAGC | 7 |
| flgB-F | GCGTTCAGCAACATGTCTGTTTCTCGACAAGGATATTGAGG | 16 |
| fliH-R | GCAGCTGCTTGTACGTTGATCCGTACCGTTTATACGAGTC | 17 |
| aprEclone-fF | TCTGATGTCTTTGCTTGGCG | 18 |
| aprEclone-fR | ACAGACATGTTGCTGAACGC | 19 |
| aprEclone-bF | ATCAACGTACAAGCAGCTGC | 20 |
| aprEclone-bR | CTGATTGGGTAGGATCCGCGCCATTATGTCATGAAGCACG | 21 |
| aprEclone-mF | GAGTCAATTCCGCTGTCGTTCTCACGGTACGCATGTAG | 22 |
| aprEclone-mR | AGAATTAACGCTGCTGCTCC | 23 |
| aprEclone-checkF | TTGCAAATCGGATGCCTGTC | 24 |
| aprEclone-checkR | TATTGTGGGATACGACGCTG | 25 |

<Preparation of Donor DNA>

By using the chromosomal DNA of the strain 168 (aprE::spec, lacI, Pspac-chpA) obtained in Example 2 as a template, a DNA fragment was amplified by PCR using APNC-F primer (SEQ ID NO: 7) and chpA-R primer (SEQ ID NO: 6) (see FIG. 5). The amplified DNA fragment was referred to as selectable marker gene cassette.

In addition, the flgB-fliH region (desired DNA sequence), the 5'-outside-region (fragment A) of the target region for deletion, 3'-outside-region (fragment B) of the target region for deletion and the first homologous recombination region (fragment C) were amplified by PCR from the chromosomal DNA of Bacillus subtilis 168 using primer sets of flgB-F (SEQ ID NO: 16) and fliH-R (SEQ ID NO: 17), aprEclone-fF (SEQ ID NO: 18) and aprEclone-fR (SEQ ID NO: 19), aprEclone-bF (SEQ ID NO: 20) and aprEclone-bR (SEQ ID NO: 21), and aprEclone-mF (SEQ ID NO: 22) and aprEclone-mR (SEQ ID NO: 23), respectively (see FIG. 7(i)).

Using the thus-obtained PCR fragments, i.e. the selectable marker gene cassette, the 5'-outside-region (fragment A), the flgB-fliH region (desired DNA sequence), the 3'-outside-region (fragment B) and the first homologous recombination region (fragment C), SOE-PCR (Gene, 77, 61 (1989)) were performed with the primer set of aprEclone-fF (SEQ ID NO: 18) and aprEclone-mR (SEQ ID NO: 23). As a result, a DNA fragment which has the 5'-outside-region (fragmentA), the flgB-fliH region (desired DNA sequence), the 3'-outside-region (fragment B), the selected marker gene cassette and the first homologous recombination region (fragment C) aligned in that order, was obtained as shown in FIG. 7(i). This DNA fragment was used in the following transformation as a donor DNA.

<Transformation>

1. First Homologous Recombination

The transformation (first homologous recombination) and the selection of transformants after the first homologous recombination were performed in a similar manner to Example 1 above.

2. Second Homologous Recombination

The transformant having the spectinomycin resistance was cultured overnight in LB liquid medium. After dilution of the culture, the culture solution was applied on a LB medium plate supplemented with 1 mM IPTG. As a result, 100 or more colonies were obtained. These colonies growing on IPTG-containing LB medium plate are the Bacillus subtilis transformants. In the transformant, the flgB-fliH region (desired DNA sequence) was inserted into the target region for replacement in the host DNA and the selectable marker gene cassette was deleted from the host DNA through the second homologous recombination (see FIG. 7(iii) to (iv)).

Further, for confirming the insertion of the flgB-fliH region (desired DNA sequence) and the deletion of the selectable marker gene cassette, the obtained 24 single colonies of Bacillus subtilis transformants were examined by PCR using aprEclone-checkF primer (SEQ ID NO: 24) and aprEclone-checkR primer (SEQ ID NO: 25). As a result, all 24 transformants have no selectable marker gene cassette and have the flgB-fliH region.

As is apparent from the above results, it is possible to introduce the desired DNA sequence into the target region for replacement in Bacillus subtilis genome at high accuracy by the method of the present invention using the donor DNA and the selectable marker cassette contained therein.

Further, neither the spectinomycin-resistance gene nor the kanamycin-resistance gene used in the transformation steps as the selectable marker gene remains in the resultant transformant. Therefore, the transformant obtained by the method of the present invention can be repeatedly used for further transformation with the spectinomycin-resistance gene or the kanamycin-resistance gene as the selectable marker gene.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119(a) on Patent Application No. 2008-076008 filed in Japan on Mar. 24, 2008, and Patent Application No. 2009-044193 fled in Japan on Feb. 26, 2009, each of which is entirely herein incorporated by reference.

What is claimed is:

1. A method of deleting a target region in a host DNA using a donor DNA:
   wherein the donor DNA comprises regions homologous to
   (a) a 5'-side region outside of the target region in the host DNA,
   (b) a 3'-side region outside of the target region in the host DNA and
   (c) a first homologous recombination region inside of the target region in the host DNA,
   wherein (a), (b) and (c) are, respectively, in that order,
   and, between the region homologous to the 3'-side region and the region homologous to the first homologous recombination region further comprises a first selectable marker gene, an expression-inducing promoter and a second selectable marker gene, wherein the second selectable marker gene is expressed under the control of the expression-inducing promoter;
   which method comprises the steps of:
   a first step of performing homologous recombination between the donor DNA and the host DNA at the regions of the 5'-side region and the first homologous recombination region, to conduct selection of a host integrated with the donor DNA based on expression of the first selectable marker gene; and
   a second step of performing homologous recombination, within the host DNA integrated with the donor DNA by the first step, between the 3'-side region derived from the host DNA and the 3'-side region derived from the donor DNA,
   inducing expression of said second selectable marker gene, and
   selecting a host whose target region is deleted based on a lack of expression of the second selectable marker gene under an expression-inducing condition for the expression-inducing promoter,
   wherein said second selectable marker gene does not remain in said host DNA after said second step of performing homologous recombination.

2. A method of producing a host, wherein said host is produced by deleting a target region for deletion in the host DNA using the method according to claim 1.

3. The method of deleting a target region in a host DNA according to claim 1, wherein, in the second step, the host whose target region is modified is selected by positive selection based on expression of the second selectable marker gene.

4. The method of deleting a target region in a host DNA according to claim 3, wherein the second selectable marker gene is a gene encoding a protein that induces death of a host cell.

5. The method of deleting a target region in a host DNA according to claim 4, wherein the second selectable marker gene is a chpA gene.

6. The method of deleting a target region in a host DNA according to claim 5, wherein the expression-inducing promoter is a promoter which induces expression of a downstream gene in the presence of an expression inducer.

7. The method of deleting a target region in a host DNA according to claim 6, wherein the first selectable marker gene is a drug-resistance gene.

8. The method of deleting a target region in a host DNA according to claim 7, wherein the host is Bacillus subtilis.

9. A method of producing a host, wherein said host is produced by deleting a target region for deletion a target region for deletion in the host DNA using the method according to any one of claims 3-8.

* * * * *